United States Patent
DiChiara (12)

(10) Patent No.: US 6,270,216 B1
(45) Date of Patent: Aug. 7, 2001

(54) EYEGLASS FRAME SHIELD AND FASTENER

(76) Inventor: Carmine S. DiChiara, 23 Gregory La., Warren, NJ (US) 07059

(*) Notice: Subject to any disclaimer, the term of this patent is extended or adjusted under 35 U.S.C. 154(b) by 0 days.

(21) Appl. No.: 09/418,756

(22) Filed: Oct. 15, 1999

(51) Int. Cl.[7] ................................. G02C 7/10; A61F 9/02
(52) U.S. Cl. ................................. 351/44; 351/121; 2/449
(58) Field of Search ........................... 351/44, 111, 116, 351/121; 2/13, 448, 449, 450, 451

(56) References Cited

U.S. PATENT DOCUMENTS

| | | | |
|---|---|---|---|
| 1,138,012 | 5/1915 | Perkins | 351/111 |
| 2,688,272 | 9/1954 | Bailey | 351/111 |
| 3,052,159 | 9/1962 | Gross et al. | 351/111 |
| 3,052,161 | 9/1962 | Berend | 351/41 |
| 3,165,754 | 1/1965 | Rodgers, Jr. et al. | 351/47 |
| 3,505,679 | 4/1970 | Bennett | 351/44 |
| 3,721,490 | 3/1973 | Prince | 351/44 |
| 4,105,304 | 8/1978 | Baker | 351/47 |
| 4,785,481 | 11/1988 | Palmer, III et al. | 2/436 |
| 5,033,837 | 7/1991 | Leonardi | 351/121 |
| 5,080,476 | 1/1992 | Monin | 351/119 |
| 5,347,325 | 9/1994 | Lei | 351/118 |
| 5,543,864 | 8/1996 | Hirschman et al. | 351/47 |
| 5,548,351 | 8/1996 | Hirschman et al. | 351/47 |
| 5,608,469 | 3/1997 | Bollé | 351/44 |
| 5,668,619 | 9/1997 | Bollé | 351/118 |
| 5,798,815 | 8/1998 | Hirschman et al. | 351/44 |

OTHER PUBLICATIONS

Titmus Corporation, T–LOC Brochure, Oct., 1999.*

\* cited by examiner

*Primary Examiner*—Huy Mai
(74) *Attorney, Agent, or Firm*—Roylance, Abrams, Berdo & Goodman, L.L.P.

(57) ABSTRACT

An eyeglass frame assembly having a shield for attachment to an eyeglass frame with the use of a fastener. The shield has two shoulders forming a passageway for a temple piece of the eyeglass frame. The fastener, when tightened, clamps the shoulders against the temple piece to rigidly connect the shield to the eyeglass frame and prohibit relative movement between the shield and the frame. The fastener can have a frangible portion that is removable after the application of a predetermined force resulting in a non-removable security-type screw. Alternatively, the fastener can be a common screw or a common bolt having either common nuts or gripping lock nuts.

20 Claims, 5 Drawing Sheets

EYEGLASS FRAME SHIELD AND FASTENER

FIELD OF THE INVENTION

The present invention generally relates to eyeglass frames and attachments thereto such as shields. More specifically, the present invention relates to a shield for attaching to a temple piece of eyeglass frames to protect the eyes of the user. The shield is rigidly attached in a clamping fashion by a fastener. The present invention also relates to a fastener for use with eyeglass frames and their attachments wherein the fastener has a frangible portion capable of being broken off from a main portion after applying a predetermined force to the frangible portion in order to form a security screw that is not easily removed.

BACKGROUND OF THE INVENTION

It is often desired to apply safety shields to eyeglasses in order to protect the user from debris that can contact the eye from the top or sides of the eyeglasses. Typically, these shields are either too loosely connected to provide adequate protection in all circumstances or are rigidly applied to the temple pieces in a relatively elaborate manner in an eyeglass factory, requiring specialized equipment. Often it is desired to retrofit eyeglasses with rigid safety shields in the field, away from specialized equipment and eyeglass factories. Although attempts have been made in the past to provide safety shields to eyeglasses without specialized equipment and away from eyeglass factories, the resulting safety shield is generally too loosely attached to the eyeglasses, the connection is not sufficiently durable, or the temple must be especially manufactured or subject to damage in order to receive the shield.

Additionally, safety directors charged with ensuring that employees wear eyeglasses with safety shields are presented with the problem of equipping non-conforming employees with permanent eyeglass safety shields in a quick, efficient, and cost-effective manner. Previous safety shields can not be attached permanently to eyeglasses in a quick, efficient, and cost-effective manner.

Examples of these prior eyeglass frames are disclosed in the following U.S. Pat. Nos.: 5,798,815 to Hirschman et al.; U.S. Pat. No. 4,105,304 to Baker; and U.S. Pat. No. 3,505,679 to Bennett.

Thus, there is a continuing need to provide improved eyeglass frames with rigidly attached shields that can be easily attached to existing eyeglasses.

SUMMARY OF THE INVENTION

Accordingly, it is a primary object of the invention to provide improved shield for attachment to a temple piece of eyeglasses.

Another object of the invention is to provide an improved shield which is easy to install.

Still another object of the invention is to provide a shield that is rigidly and permanently connected to the temple piece while not destroying the eyeglasses or the temple pieces.

Another object of the invention is to provide a fastener for attaching the shield wherein the fastener can be applied with ordinary tools but that provides a substantially permanent, rigid connection between the shield and the eyeglass.

The foregoing objects are basically attained by providing a shield for an eyeglass frame, comprising: a main member for protecting an eye of the user of the shield; a first shoulder extending from the main member, the first shoulder having a first hole having a first axis and extending completely through the first shoulder; a second shoulder spaced from the first shoulder and extending from the main member, the second shoulder having a second hole being coaxial with the first hole and extending completely through the second shoulder; and an elongated passageway positioned between the first and second shoulders and extending along a second axis, which is substantially perpendicular to the first axis and which is spaced from the first axis.

The foregoing objects are also attained by providing An eyeglass frame assembly, comprising: a first temple piece; a first shield coupled to the first temple piece, the first shield having a main member for protecting an eye of the user of the first shield, a first shoulder extending from the main member, the first shoulder having a first hole having a first axis and extending completely through the first shoulder, a second shoulder spaced from the first shoulder and extending from the main member, the second shoulder having a second hole being coaxial with the first hole and extending completely through the second shoulder, and an elongated passageway positioned between the first and second shoulders and extending along a second axis, which is substantially perpendicular to the first axis and which is spaced from the first axis; and a fastener extending through both the first and second holes and coupling the first and second shoulders together, the first temple piece being positioned within the passageway and between the first and second shoulders.

The objects are still further achieved by providing an eyeglass frame assembly, comprising: an eyeglass frame; an supplemental element for coupling to the eyeglass frame; and a fastener secured to the supplement element for coupling the supplemental element to the eyeglass frame, the fastener having a body, an inner head, and an outer head, the outer head being capable of separation from the body and the inner head upon the application of a predetermined force to the outer head.

Other objects, advantages, and salient features of the invention will become apparent from the following detailed description, which, taken in conjunction with the annexed drawings, discloses preferred embodiments of the invention.

DRAWINGS

Referring now to the drawings which form a part of this original disclosure.

DETAILED DESCRIPTION OF THE INVENTION

Referring to FIGS. 1–4, an eyeglass frame assembly 4 in accordance with a first embodiment of the invention is illustrated. Eyeglass frame assembly 4 includes an eyeglass frame 10, shields 6 and 7 for protecting the eyes of the user, and fasteners 8 for clamping shields 6 and 7 to eyeglass frame 10. The invention permits the shields 6 and 7 to be rigidly and securely fastened to the frame 10 through the use of ordinary tool such as screwdrivers, allowing the shields 6 and 7 to be attached in the field or anywhere the user may suddenly require, and with a fastener 8 that clamps the frame 10 without damage to the frame 10, in the event that the shields 6 and 7 should later be removed, and with a fastener 8 that can, optionally, prohibit removal from the clamped position.

Figure 1:
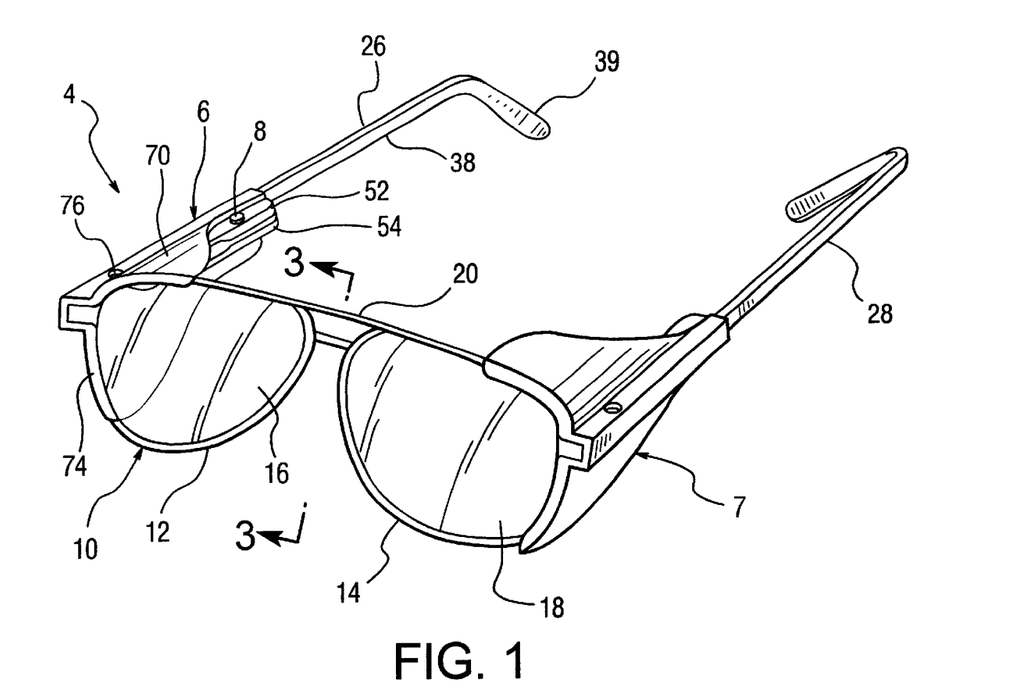
FIG. 1 is a front, top, side elevation view of an eyeglass frame assembly with shields in accordance with a first embodiment of the present invention.
Figure 2:
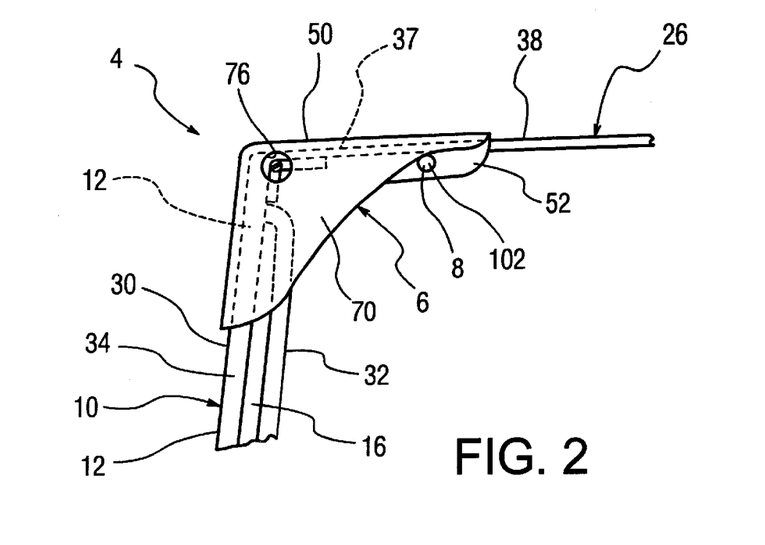
FIG. 2 is a partial, top view of the eyeglass frame assembly illustrated in FIG. 1.
Figure 3:
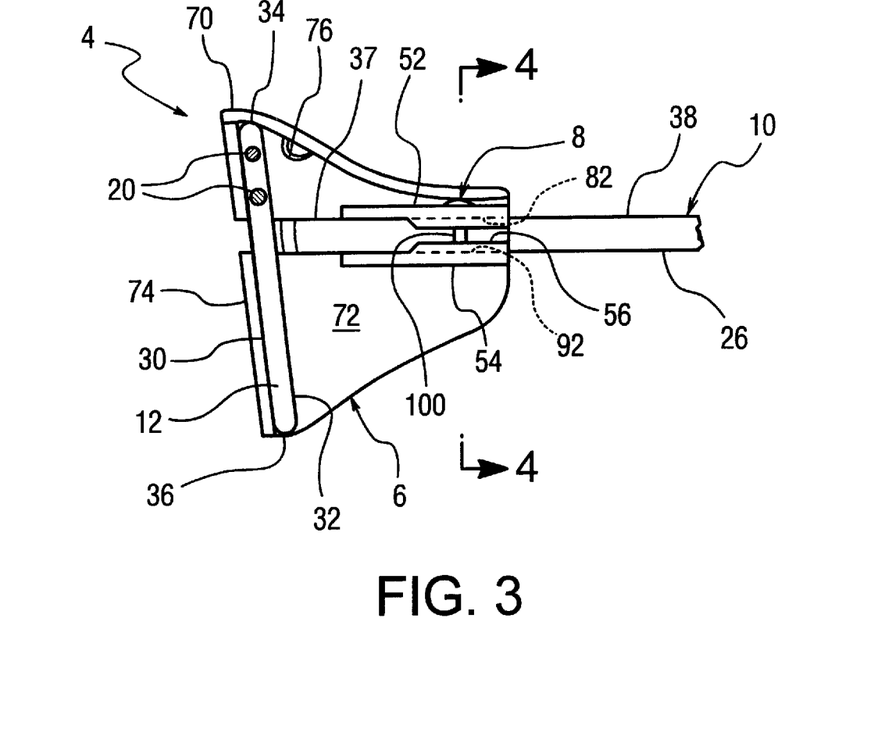
FIG. 3 is a partial, cross-section view of the eyeglass frame assembly illustrated in FIG. 1, taken along line 3—3.
Figure 4:
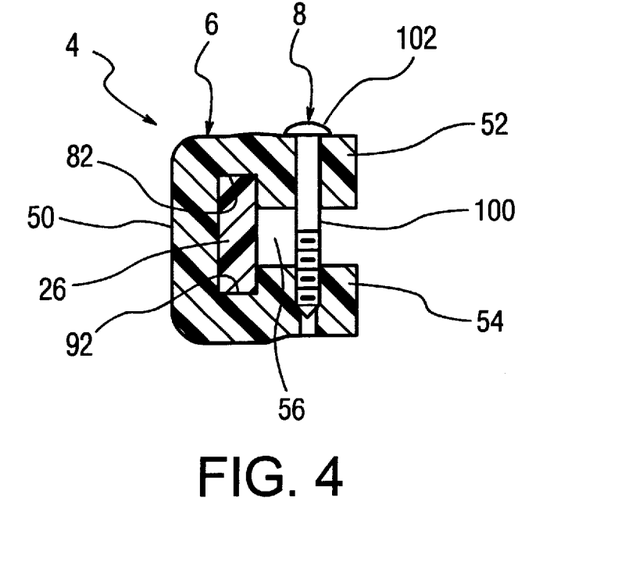
FIG. 4 is an enlarged, cross-sectional view of the shield and temple piece illustrated in FIG. 3, taken along line 4—4.
Figure 5:
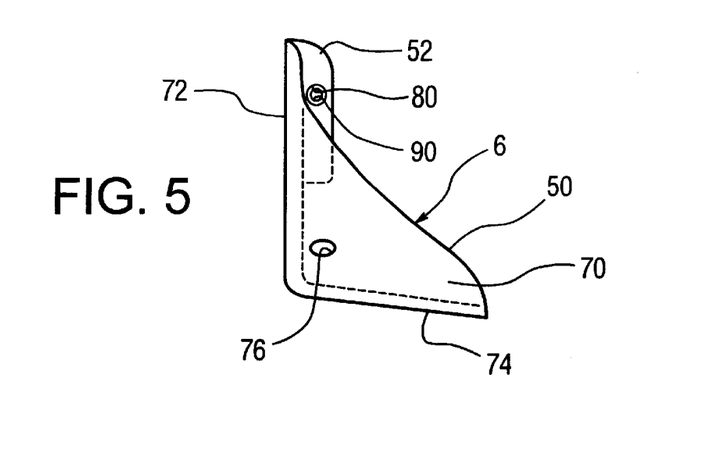
FIG. 5 is a top view of a shield in accordance with the first embodiment of the present invention, detached from eyeglasses.
Figure 6:
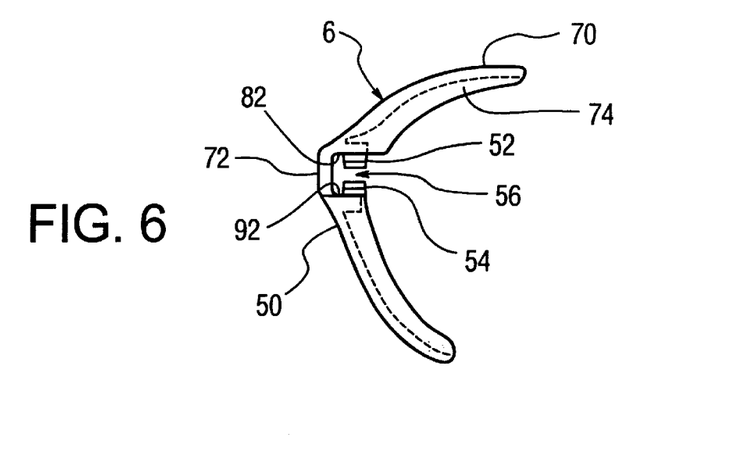
FIG. 6 is a front view of a shield in accordance with the first embodiment of the present invention, detached from eyeglasses.
Figure 7:
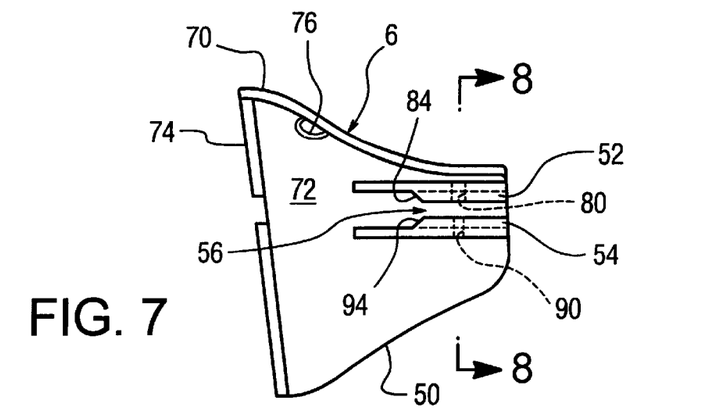
FIG. 7 is an inner side view of a shield in accordance with the first embodiment of the present invention, detached from eyeglasses.
Figure 8:
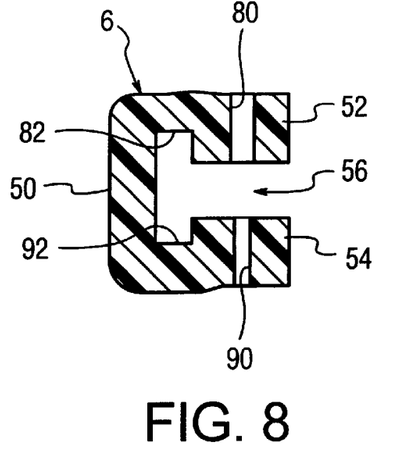
FIG. 8 is enlarged, cross-sectional view of the shield illustrated in FIG. 7, taken along line 8—8.

Eyeglass frame 10 comprises two cylindrical rims 12 and 14 supporting eyepieces or lenses 16 and 18. Eyeglass frame 10 further comprises a bridge 20, and two temple pieces 26 and 28.

Lenses 16 and 18, temple pieces 26 and 28, and bridge 20 as well as the connections pertaining to these elements are conventional and known in the art. Accordingly, these elements will only be briefly described herein.

Rims 12 and 14 surround and support lenses 16 and 18 in a secure manner that is well-known in the art. Each of rims 12 and 14 has a front 30, a rear 32, a top 34, and a bottom 36. Although rims 12 and 14 are shown as completely encompassing the perimeter of lenses 16 and 18, respectively, it should be understood that rims 12 and 14 can be adapted to only partially encompasses lenses 16 and 18 as is known in the art. Bridge 20 connects rims 12 and 14 and helps support rims 12 and 14 in position on the face of the user. Bridge 20 can be formed of any known material. Additionally, bridge 20 can be formed of twisted strands of cable as discussed in U.S. Pat. No. 5,801,806 to DiChiara, the disclosure of which is incorporated herein by reference thereto.

Although rims 12 and 14 have been illustrated as being of a generally oval shape, it should be understood that rims 12 and 14 can take any shape desired that can support and retain lenses 16 and 18. Additionally, lenses 16 and 18 may be either prescription lenses or non-prescription lenses such as common sunglass lenses. Also lenses 16 and 18 can be lenses for use as safety lenses for eye protection in hazardous situations.

Temple pieces 26 and 28 are attached to rims 12 and 14, respectively, and are preferably hook-shaped to be positioned behind the ears of the user. It should be understood that temple pieces 26 and 28 can take any configuration that suitably supports eyeglass frame 10 on the user's head. For instance, temple pieces 26 and 28 can be substantially straight. Although temple pieces 26 and 28 are illustrated as being attached to rims 12 and 14, temple pieces 26 and 28 can be attached to lenses 16 and 18 in any known manner, including attachment without the use of rims 12 and 14, or directly to the lens or lenses. Additionally, although as illustrated, temple pieces attach two lenses 26 and 28 to a face of a user, temple pieces 26 and 28 can be used with only one lens or any type of eyewear or face protection requiring attachment to the head of the user.

Each temple piece 26 and 28 is substantially identical in function and structure except for being mirror images of one another such that they can attach to opposite sides of the rims 12 and 14 and to opposite sides of the head of the user. Accordingly, only one temple piece 26 will be described in detail.

Temple piece 26 includes a rim engaging section 37, a middle section 38, and an ear engaging section 39. Rim engaging section 37 has a lug 70 for attaching to lens 16 and/or rim 12 in a known manner. Rim engaging section 37 can connect to lens 16 and/or rim 12 in any known manner.

Ear engaging section 39 can be curved to fit snugly around the back of the user's ear to hold the frame 10 properly on the user's face. The ear engaging section 39 can be any known ear engaging portion and formed of a variety of known materials; such as those that are generally straight with rubber protrusions to frictionally engage the head of the user above the ear and not behind the ear.

Middle section 38 is typically rectangular in cross-section, but can be made of any shaped cross-section. Additionally, middle section 38 can be formed of any of a variety of known materials; such as, plastic, metal, and composites. Also, middle section 38 can be formed of twisted strands of cable as described in applicant's co-pending patent application Ser. No. 09/387,265, filed Aug. 31, 1999, which is incorporated herein by reference.

Shields 6 and 7 are substantially identical except that one is the mirror image of the other. Accordingly, only one shield 6 will be described in detail.

As seen in FIGS. 5–8, shield 6 has a main member 50, a first, upper shoulder 52, a second, lower shoulder 54, and a passageway 56 extending between the two shoulders 52 and 54. Shield 6 is preferably integrally formed as a one-piece, unitary member, although it can be formed from a number of different parts connected together with fasteners. Preferably, shield 6 is preferably made from molded plastic material, but can be made from other materials as well as known in the art, such as metal or composites. Also, shield 6 is preferably transparent to permit peripheral vision, although shield 6 can be translucent or opaque.

Main member 50 preferably has a top wall 70, sidewall 72, and front wall 74 as generally known in the art to seal the areas around the connection between the temple pieces 26 and 28 and the rim 14. Main member 50 also has an access opening 76 extending completely through the main member 50 to provide access by a screwdriver to the screws used in connection with the hinge coupling the temple pieces 26 and 28 to rim 14. If desired, main member 50 can be formed without top wall 70 and/or front wall 74, leaving only sidewall 72 as the protective shielding.

Upper shoulder 52 extends from main member 50 in a cantilevered manner and in a substantially perpendicular manner and has a hole 80, an elongated depression or indent 82, and a recess area 84. Hole 80 extends completely through shoulder 52 for receiving fastener 8 and is preferably a through-hole, with no threads, sized to permit fastener 8 to be freely inserted therein and to provide for the clamping action discussed below. Indent 82 extends along the length of the shoulder for receiving the upper edge of temple piece 26. Indent 82 is formed such that the portion of the shoulder 52 furthest from the indent 82 overhangs the indent 82, permitting the shoulder to prohibit the temple piece 26 from moving out of the indent 82 in a direction substantially perpendicular to the longitudinal axis of temple piece 26. Recess area 84 is a thinned area of the shoulder to permit access for temple piece/spring hinge hardware, if needed. Thus, shield 6 can fit frames 10 having traditional hinges or spring hinges.

Lower shoulder 54 is substantially identical to upper shoulder 52 except that it is a mirror image of upper shoulder 52 and except for the hole 90. Lower shoulder 54 extends from main member 50 in a cantilevered manner and in a substantially perpendicular manner and has a hole 90, an elongated depression or indent 92, and a recess area 94. Hole 90 extends completely through shoulder 54 for receiving fastener 8 and is coaxial with hole 80. Hole 90 preferably has a smaller diameter than hole 80 to permit fastener 8 to be guided and be easily inserted into the hole 90. Preferably, hole 90 has no threads thereby providing fastener 8 with the ability to cut its own threads in order to have a more secure connection. Therefore, hole 90 preferably has a smaller diameter than hole 80. Alternatively, hole 90 could be sized and have threads to mate with those of fastener 8. As discussed, below, there are numerous alternatives and options in the manner in which shoulders 52 and 54 are clamped by a fastener. Fastener 8 can be a self tapping screw, a traditional screw, a bolt with a common nut or a lock nut, or take another form, with the shoulders 52 and 54 being adapted to accommodate the fastener desired.

Indent 92 extends along the length of the shoulder 54 for receiving the lower edge of temple piece 26. Indent 92 is formed such that the portion of the shoulder 54 furthest from the indent 92 overhangs the indent 92, permitting the shoulder 54 to prohibit the temple piece 26 from moving out of the indent 92 in a direction substantially perpendicular to the longitudinal axis of temple piece 26. Recess area 94 is a thinned area of the shoulder to permit access for temple piece/spring hinge hardware, if needed.

Although indents 82 and 92 are shaped to correspond to and receive temple pieces having rectangular cross-sections, indents 82 and 92 will nonetheless secure temple pieces of different sizes and cross-sectional shapes. Also, indents can take different shapes to correspond and receive temple pieces of any of a variety of shapes and sizes.

Figure 9:
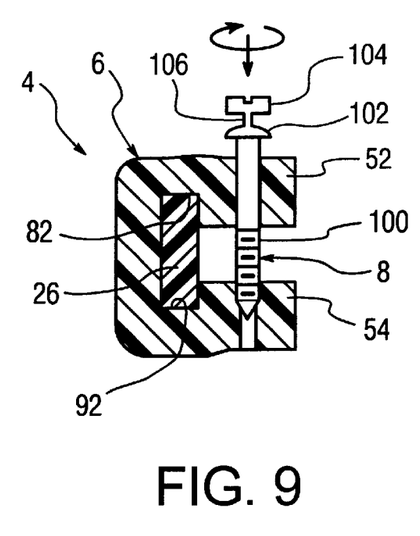
FIG. 9 is enlarged, cross-sectional view of the shield, eyeglasses and fastener similar to FIG. 4 but illustrating a partially inserted fastener in accordance with a first embodiment of the invention.
Figure 10:
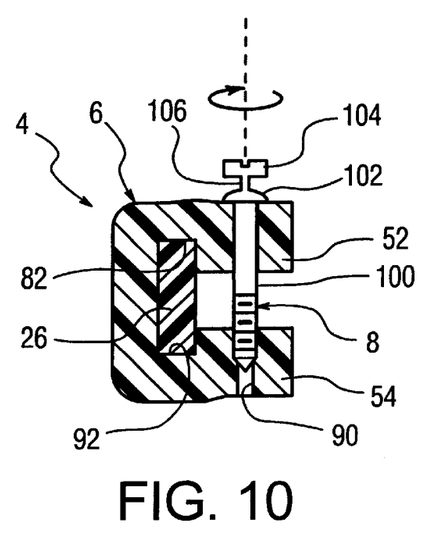
FIG. 10 is enlarged, cross-sectional view of the shield, eyeglasses and fastener similar to FIG. 4 but illustrating a fully inserted fastener in accordance with a first embodiment of the invention with the outer head still attached to the inner head.
Figure 11:
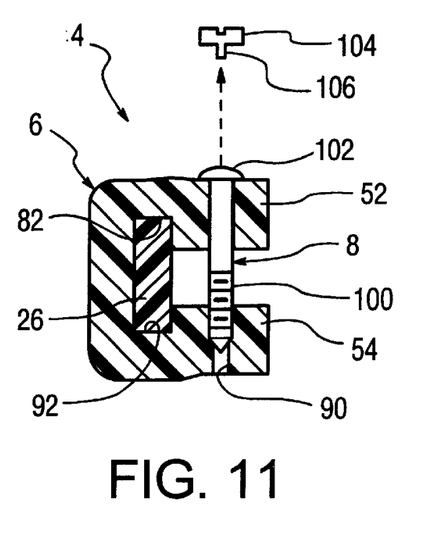
FIG. 11 is enlarged, cross-sectional view of the shield, eyeglasses and fastener similar to FIG. 4 but illustrating a fully inserted fastener in accordance with a first embodiment of the invention with the outer head of the fastener removed after the application of a predetermined force to the outer head in a rotational direction.

As seen in FIGS. 9–11, fastener or screw 8 preferably has a body 100, an inner head 102 and an outer head 104. Body 8 is a screw with threads that are capable of forming their own threads in shoulder 54 when turned. Inner head 102 is directly attached to body 100 and outer head 104 is attached to inner head 102 by an attaching element 106. Outer head 104 preferably has a slot or slots for receiving a tool such as a screwdriver for rotating and driving screw 8. Alternatively, head 104 can be formed in other known manners; such as, a safety screw head wherein only rotation in one direction is permitted or as a multi-sided head for receiving a socket or wrench, for example, a hex-head. Fastener 8 is preferably formed from metal, such as nickel silver, but can be formed of other materials, if desired.

Attaching element 106 is formed to withstand the force applied by the screwdriver, wrench or other tool in driving screw 8 into shoulders 52 and 54 to clamp shoulders 52 and 54 around temple piece 26 to rigidly and permanently clamp temple piece 26 within passageway 56 and rigidly and permanently connect shield 6 to frame 10. But attaching element 106 is also formed to fail at a predetermined force so that outer head 104 can be removed from screw 8 once screw 8 is sufficiently tightened to clamp shoulders 52 and 54 and relative movement between shield 6 and frame 10 is prohibited. That is, once screw 8 is tightened completely in shoulders 52 and 54, further application of a rotational force beyond that which was necessary to fully clamp the shoulders 52 and 54 will break the attaching element 106 and snap off the outer head 104. Thus, attaching element 106 is designed to fail after application of a predetermined moment or rotation force is applied to outer head 104, that predetermined force being greater than the force necessary to fully drive the screw 8 into the shoulders 52 and 54 as necessary. Alternatively, the predetermined force referred to above can be accomplished by clipping off the outer head 104 with, for example, a tool such as a pliers. The force necessary to clip off the outer head 104 is preferably insufficient to disturb in any way the connection between fastener 8 and the upper and lower shoulders 52 and 54. Further the clipping off of the outer head 104 can be accomplished by cutting the attaching element between said outer head 104 and the inner head 102.

Once outer head 104 snaps off, only inner head 102 remains connected to the body 100 and inner head is preferably designed with a relatively smooth, exposed surface that does not have access areas for tools to remove or unscrew screw 8. Therefore, screw 8 becomes a security screw once outer head 104 is removed.

In use, the invention permits the user of an ordinary frame, not particularly made for receiving attachments such as shield 6, to attach a safety shield easily and quickly with a screwdriver, wrench or other appropriate tool suitable for the type of fastener head employed. Shield 6 is slid or snapped onto temple piece 26 so that temple piece sits within indents 82 and 92. The shield 6 is then slid to the appropriate position, if necessary, such that the walls 70, 72 and 74 are properly positioned relative to frame 10 to provide maximum protection. Then fastener 8 is inserted into hole 80 and, with a tool, fastener 8 is driven into hole 90 to clamp shield 6 against temple piece 26 to prohibit relative movement between the shield 6 and temple piece 26 and to form a substantially rigid connection there between. When such connection is made, further turning of the tool on the outer head 104 of fastener 8 removes outer head 104, leaving screw fully inserted into the shoulders 52 and 54, but incapable of being easily removed without destroying fastener 8. Alternatively, the outer head 104 is clipped off instead of attempting further rotation of the outer head 104. The protective eyeglass frame assembly 4 is then complete. If it is necessary to remove shield 6, fastener is destroyed and shield 6 can be removed by sliding or snapping off. Then, frame 10 can be used as originally used, and without damage to the frame.

It should be understood that the manner of clamping the shield 6 on the frame 10 with fastener 8 is not limited merely to shields, and can be used with other attachments to eyeglass frames. Also, fastener 8 is not limited merely to clamping shoulders but can be used for other purposes, such as, connecting the hinges forming the attachment of the temple pieces and the rim, or for tightening a rim around lenses, or for attaching additional elements to eyeglasses, for example, nose guards.

Figure 12:
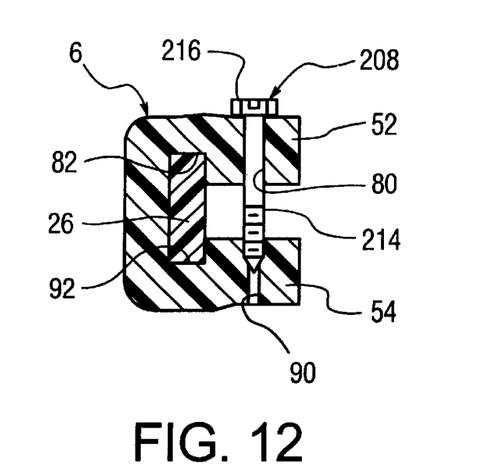
FIG. 12 is enlarged, cross-sectional view of the shield, eyeglasses and fastener similar to FIG. 4 but illustrating a fully inserted fastener with no frangible portions in accordance with a second embodiment of the invention.

In FIG. 12, fastener 208 is another fastener option in accordance with a second embodiment of the present invention. Fastener 208 can be used with shield 6 and frame 10 as disclosed above. Fastener 208 differs from fastener 8 only in that fastener 208 is a common screw that has a slotted head 216, which does not snap off from the body 214 of the screw 208 at a predetermined force once the screw 208 is fully driven into shoulders 52 and 54.

Figure 13:
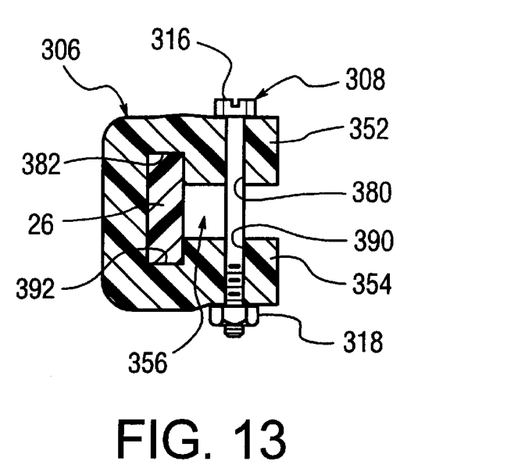
FIG. 13 is enlarged, cross-sectional view of the shield, eyeglasses and fastener similar to FIG. 4 but illustrating a fully inserted bolt-like fastener in accordance with a third embodiment of the invention.

In FIG. 13, fastener 308 is another fastener option in accordance with a third embodiment of the present invention. Fastener 308 differs from fastener 8 in that fastener 308 is a bolt with a head 316, which does not snap off from the rest of the bolt 308 at a predetermined force once the bolt 308 is fully driven. Bolt 308 uses a nut 318. Since bolt 308 passes through-holes without cutting threads, appropriate changes to the shoulders must be made. Shield 306 in FIG. 13 is substantially identical to shield 6 above except for the formation of hole 390 in shoulder 354. Hole 380 in shoulder 352 and hole 390 are both coaxial through-holes for receiving bolt 308 in a known manner.

Figures 14, 15:
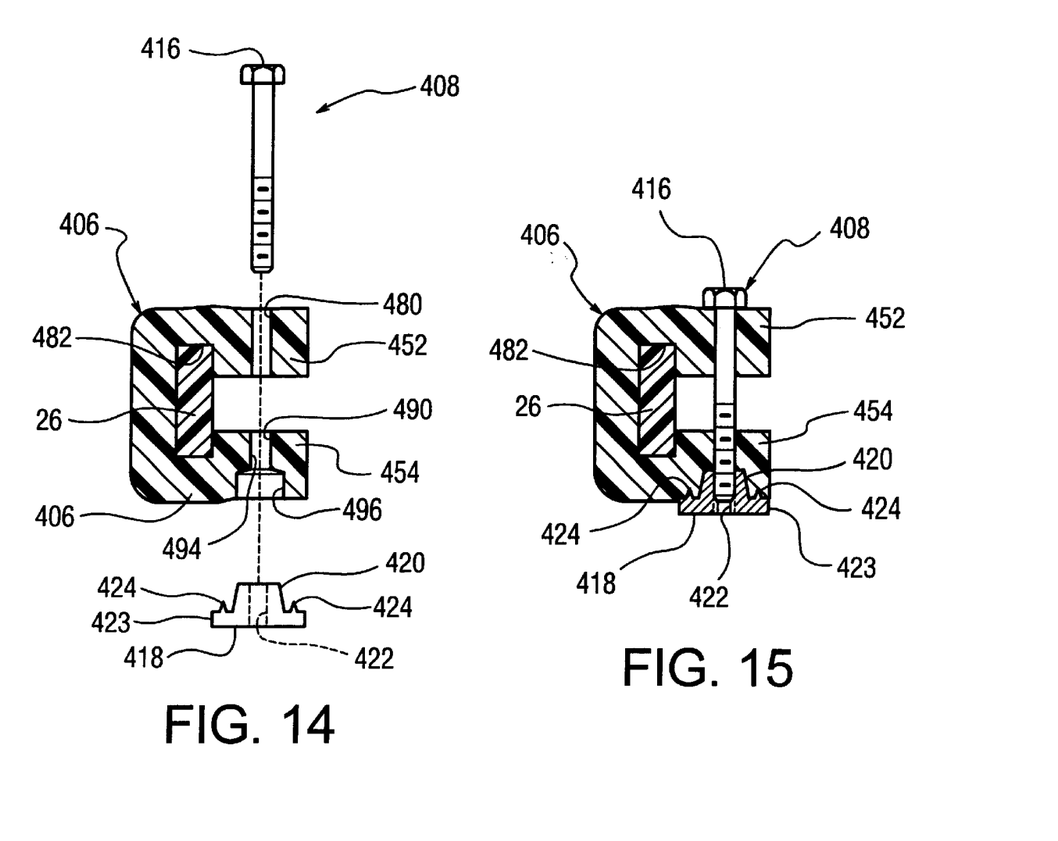
FIG. 14 is enlarged, cross-sectional view of the shield, eyeglasses and fastener similar to FIG. 4 but illustrating an exploded view of the fastener and its nut-like structure in accordance with a fourth embodiment of the invention.
FIG. 15 is enlarged, cross-sectional view of the shield, eyeglasses and fastener similar to FIG. 14 but illustrating the fastener and its nut-like structure engaged in accordance with the fourth embodiment of the invention.

In FIGS. 14 and 15, fastener 408 is another fastening option in accordance with a fourth embodiment of the present invention. Fastener 408 is substantially identical to fastener 308 above, except fastener 408 employs a lock nut 418. Nut 418 has a frustoconical section 420 with a threaded opening 422 and a flange 423 with engaging tips or spikes 424.

Shoulder 452 is substantially identical to shoulder 352. However, shoulder 454 differs from shoulder 354 in that shoulder 454 has a hole 490 with a narrow cylindrical portion 494 and a wider cylindrical portion 496. In use, lock nut 418 engages bolt 408 and is forced within wider portion 496 as the bolt is tightened. The frustoconical portion 420 is tapered to form a press fit within the cylindrical, wider portion 496 of hole 490 as they are forced into engagement. Then as the nut 418 becomes fully forced into wider portion 496, tips 424 engage and dig into shoulder 454 to create an additional securing force and form a substantially permanent clamping of the shoulders 452 and 454. Once fully installed, bolt 408 and lock nut 418 make removal of nut 418 and bolt 408 extremely difficult.

It should be understood that the heads of fasteners discussed above with respect to the additional embodiments of the invention could be common slotted heads or safety heads or multi-sided heads such as hex-heads, or any other type of fastener head. Safety heads being those fastener heads having portions that can receive a screwdriver or other tool and permit rotation of the fastener in one direction to drive and insert the fastener, but prohibits the use of the screwdriver for removing the fastener.

While advantageous embodiments have been chosen to illustrate the invention, it will be understood by those skilled in the art that various changes and modifications can be made therein without departing from the scope of the invention as defined in the appended claims.

What is claimed is:

1. A shield of an eyeglass frame, comprising:

a main member for protecting an eye of the user of the shield;

a first shoulder extending from said main member, said first shoulder having a first hole having a first axis and extending completely through said first shoulder;

a second shoulder spaced from said first shoulder and extending from said main member, said second shoulder having a second hole being coaxial with said first hole and extending completely through said second shoulder;

an elongated passageway positioned between said first and second shoulders and extending along a second axis, which is substantially perpendicular to said first axis; and a fastener for clamping said first shoulder and said second shoulder on a temple piece of the frame positioned within said passageway to resist relative movement therebetween.

2. A shield according to claim 1, wherein said main member includes a sidewall.

3. A shield according to claim 1, wherein each of said first and second shoulders has an elongated indent which is substantially parallel to said passageway for clamping a temple piece of the frame within said passageway.

4. A shield according to claim 3, wherein said main member, and said first and second shoulders are an integral, one-piece, unitary member.

5. A shield according to claim 4, wherein said main member, and said first and second shoulders are transparent plastic.

6. A shield according to claim 3, wherein said first hole has a first diameter and said second hole has a second diameter, which is smaller than said first diameter.

7. A shield according to claim 3, wherein said first hole has a first diameter and said second hole has a second diameter, which is equal to said first diameter.

8. An eyeglass frame assembly, comprising:

a first temple piece;

a first shield coupled to said first temple piece, said first shield having a main member for protecting an eye of the user of the first shield, a first shoulder extending from said main member, said first shoulder having a first hole having a first axis and extending completely through said first shoulder, a second shoulder spaced from said first shoulder and extending from said main member, said second shoulder having a second hole being coaxial with said first hole and extending completely through said second shoulder, and an elongated passageway positioned between said first and second shoulders and extending along a second axis, which is substantially perpendicular to said first axis; and a fastener extending through both said first and second holes and coupling said first and second shoulders together, said first temple piece being positioned within said passageway and clamped between said first and second shoulders to resist relative movement therebetween.

9. An assembly according to claim 8, wherein
each of said first and second shoulders has an elongated indent which is substantially parallel to said passageway, and said first temple piece is clamped within each of said indents and rigidly secured relative to said first shield.

10. An assembly according to claim 8, further comprising:
a transparent element coupled to said first temple piece.

11. An assembly according to claim 10, wherein
said transparent element is a lens.

12. An assembly according to claim 10, wherein
said main member includes a top wall, a sidewall, and a front wall for providing protection at the juncture of said transparent element and said first temple piece.

13. An assembly according to claim 8, wherein
said main member, and said first and second shoulders are an integral, one-piece, unitary member.

14. An assembly according to claim 8, further comprising:
a second temple piece coupled to said transparent member; and
a second shield coupled to said second temple piece.

15. An assembly according to claim 8, wherein
said fastener is a screw.

16. An assembly according to claim 15, wherein
said fastener has a body, an inner head, and an outer head, said outer head being capable of separation from said body and said inner head upon the application of a predetermined force.

17. An eyeglass frame assembly, comprising:
an eyeglass frame;
a supplemental element for coupling to said eyeglass frame; and
a fastener secured to said supplemental element for coupling said supplemental element to said eyeglass frame, said fastener having a body, an inner head, and an outer head, said outer head being capable of separation from said body and said inner head upon the application of a predetermined force to said outer head.

18. An assembly according to claim 17, wherein
said outer head is adapted for receiving a tool and is directly attached to said inner head by an attaching element formed of a predetermined thickness for separating said inner and outer heads.

19. An assembly according to claim 18, wherein
said inner head is completely, substantially smooth around said attaching element.

20. An assembly according to claim 17, wherein
said eyeglass frame includes a first temple piece; and
said supplemental element is a first shield coupled to said first temple piece, said first shield having a main member for protecting an eye of the user of the first shield, a first shoulder extending from said main member, said first shoulder having a first hole having a first axis and extending completely through said first shoulder, a second shoulder spaced from said first shoulder and extending from said main member, said second shoulder having a second hole being coaxial with said first hole and extending completely through said second shoulder, and an elongated passageway positioned between said first and second shoulders and extending along a second axis, which is substantially perpendicular to said first axis, and said fastener extends through both said first and second holes and couples said first and second shoulders together,
said first temple piece being positioned within said passageway and clamped between said first and second shoulders.

\* \* \* \* \*